United States Patent
Rebala

(10) Patent No.: US 10,060,074 B2
(45) Date of Patent: Aug. 28, 2018

(54) PEST REPELLENT FABRIC AND FUMIGANT FOR FOOD

(71) Applicant: Sudhir Reddy Rebala, Chennai (IN)

(72) Inventor: Sudhir Reddy Rebala, Chennai (IN)

(73) Assignees: ROMIN GUARD CORP., San Juan Capistrano, CA (US); PATNSTR, APC, San Juan Capistrano, CA (US)

( * ) Notice: Subject to any disclaimer, the term of this patent is extended or adjusted under 35 U.S.C. 154(b) by 0 days.

(21) Appl. No.: 15/174,703

(22) Filed: Jun. 6, 2016

(65) Prior Publication Data

US 2016/0355975 A1 Dec. 8, 2016

Related U.S. Application Data

(60) Provisional application No. 62/171,878, filed on Jun. 5, 2015.

(51) Int. Cl.
| | | |
|---|---|---|
| *A01N 25/34* | (2006.01) | |
| *A01N 25/22* | (2006.01) | |
| *A01N 65/06* | (2009.01) | |
| *A01N 65/28* | (2009.01) | |

(Continued)

(52) U.S. Cl.
CPC ............ *D06M 13/03* (2013.01); *A01N 25/34* (2013.01); *A01N 65/06* (2013.01); *A01N 65/28* (2013.01); *D06M 11/13* (2013.01)

(58) Field of Classification Search
None
See application file for complete search history.

(56) References Cited

U.S. PATENT DOCUMENTS

| | | | | |
|---|---|---|---|---|
| 3,565,749 A | * | 2/1971 | Wizon | .............. C04B 35/62227 |
| | | | | 106/166.8 |
| 4,427,737 A | * | 1/1984 | Cilento | ................. A61L 15/585 |
| | | | | 428/315.7 |

(Continued)

FOREIGN PATENT DOCUMENTS

| | | | | |
|---|---|---|---|---|
| WO | WO2014/031790 A1 | * | 2/2014 | ............. A01N 35/06 |
| WO | WO 2014099821 A2 | * | 6/2014 | ............. A01N 35/06 |

OTHER PUBLICATIONS

Wijesekera, "The chemical composition and analysis of citronella oil", Journal of the National Science Council of Sri Lanka, (Jan. 1973), pp. 67-81.*

(Continued)

*Primary Examiner* — Ernst V Arnold
*Assistant Examiner* — Kyung S Chang
(74) *Attorney, Agent, or Firm* — Patnstr, APC; Tom Brody; Peter Jon Gluck, Esq.

(57) ABSTRACT

The present invention addresses the problem of food grains stocks get deteriorated due to lack of storage facilities and due to pest-rodent infestation. The degree of deterioration is high in Tropical and sub-tropical regions. The insect and rodent damage is a major issue for woolen clothing, books and beds. The present invention discloses the embodiments include a textile with pest and/or insect repellent properties comprising: (1) Mineral Compound (2) Active Ingredient and (3) Fabric. The present invention relates to the fabrics that are treated with a pest-repellent composition. The present invention relates to the pesticide treated fabric and its preparation method.

5 Claims, 1 Drawing Sheet

(51) Int. Cl.
*D06M 13/03* (2006.01)
*D06M 11/13* (2006.01)

(56) References Cited

U.S. PATENT DOCUMENTS

| | | | | |
|---|---|---|---|---|
| 2005/0069568 A1* | 3/2005 | Hallahan | ............ | A01N 43/16 |
| | | | | 424/405 |
| 2013/0251773 A1* | 9/2013 | Galiatsatos | ............ | A01N 25/18 |
| | | | | 424/403 |

OTHER PUBLICATIONS

Draxe.com, "Clove oil", ([retrieved from on-line website:http://web.archive.org/web/20140720030132/http://draxe.com/clove-oil-uses-benefits/, pp. 1-6, on-line available since Jul. 20, 2014]).*

* cited by examiner

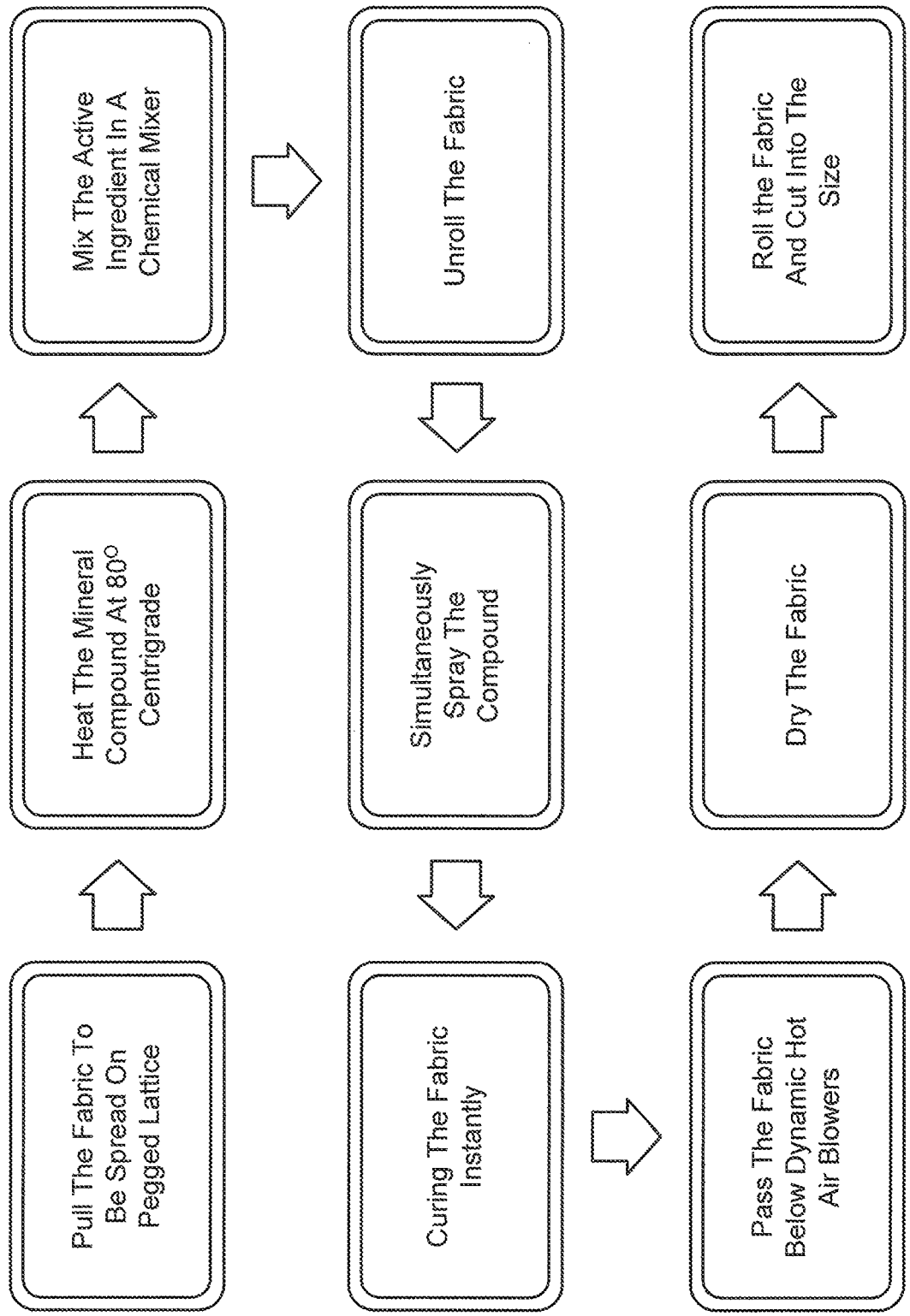

PEST REPELLENT FABRIC AND FUMIGANT FOR FOOD

CROSS REFERENCE TO RELATED APPLICATIONS

This case claims priority of U.S. Provisional Ser. No. 62/171,878 filed Jun. 5, 2015 which is assigned to the instant assignee.

Currently pest repellents are used by many farmers, gardeners, and others to protect food products, agriculture or other property. These vary in type ranging from chemical to physical. In addition to traps, devices, fabrics, or tapes are pesticides that contain synthetic chemicals or animal repellents.

Most chemically based repellents use permethrin and focus on protecting humans and pets from insects rather than pests that attack agriculture. Traps and devices such as coils are frequently ineffective. Certain insecticides such as DDT are banned. Organophosphates are harmful, as are existing fumigation agents. Additionally many fumigants are expensive as they leave a residue. Components such as malathion results in long term nerve damage, Deltamethrin poses Class II Risk and causes algal blooms, and Aluminum phosphide cause liver, kidney and lung damage. Other repellents techniques such as irradiation are temporary and expensive.

Among available repellents there is a balance between specificity and strength: the more pests that a repellent can repel, the less strength it might have. Additionally, many replants contain toxic and artificial ingredients that could be harmful to both humans specifically and the environment generally. Due to the specificity of many repellents to a specific type of pest the type treatment is also specific. Specific treatments also restrict what surfaces a treatment can be applied to.

OBJECTS AND SUMMARY

The instant disclosure relates to the fabrics that are treated with a pest-repellent composition.

The present invention relates in some embodiments to pest repellent for agriculture that can be applied in many forms. The formula can be applied to any surface. The application can include brushing, dipping soaking, spraying padding, fogging, or with foam. Embodiments of the composition are versatile. It can be deployed in many forms and is active against different types of pests including: mammals, insects and microbes.

Various objects, features, aspects, and advantages of the present invention will become more apparent from the following detailed description of preferred embodiments o the invention, along with the accompanying drawings in which like numerals represent like components.

BRIEF DESCRIPTION OF DRAWINGS

FIG. 1 Schematically depicts a substrated embodiment according to the instant teachings.

DETAILED DESCRIPTION OF THE INVENTIONS

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Embodiments of the present invention are directed towards a pest repellant for agriculture that can be applied in several forms. Embodiments of the invention may be used safely and effectively on many different surfaces. It may be used to repel the common pests that attack organically sourced material. An example of this would be effectiveness against moths that attack woolen clothing. It also protects books from bookworms and mattresses against bed bugs. Embodiments of the present invention may be safely applied directly to the skin.

Pests that are repelled include: rodents, insects of all life stages, and microbes. A non-exhaustive list of specific pests include rats, worms, ants, bed bugs, bees, cockroaches, beetles, weevils, carpet beetles, fur beetles, varied carpet beetles, spider beetles, mealworm, beetles, centipedes, flies, fruit flies, hornets, locusts, lice, moths, silverfish, woodlice, termites and ticks. The embodiments of the composition repel several types of pests through different mechanisms. Rodents, such as rats, and insects are repelled due to the composition's ability to block respiratory and pheromone systems. Insects may be destroyed due to the composition's deleterious effects on exoskeletons. Microbes, such as fungus have inhibited growth.

The composition of the present invention includes: Sesquiterpene extract of *Juniperus* bark, Curcumin treated *Eugenia Caryophyllata* oil, Sodium Chloride stabilizer, Magnesium-enriched mineral oil or its aqueous equivalent, 3(Dihydroxysilyl) Propyldimethyloctadecyl Ammonium chloride, and Mono-saturated Recinoleic Acid.

The active components are designed to repel or destroy certain pests. These include: sesquiterpene extract of *juniperus* bark (a natural extract), curcumin treated eugeniacaryophyllata oil (natural extracts), and sodium chloride stabilizer (derivative of naturally occurring salt). The remaining components form a mineral oil or aqueous solution to carry the active components. These include magnesium enriched mineral oil or its aqueous equivalent, 3(trimethoxysilyl) propyl dimethyl octadecyl ammonium chloride, and monosaturatedrecinoleic acid.

The resulting composition not only repels food pests by irritating and blocking respiratory and pheromone systems, but it is also capable of destroying the larvae, pupa or adult insects by destroying the exo-skeletal structures. The composition hinders rodents' ability to co-habit in an area that has been treated. The active ingredients also inhibit growth of microbes particularly fungus.

Embodiments of the invention affect octopamine neuroreceptors in pests that are critical for activities such as behavior, metabolism and reproduction. Disruption of these receptors disorients the pests and inhibits co-habitation. Additionally elevating enzymes in the larvae and pupae results in accelerated metamorphosis that results in interference with the exo-skeletal structure.

All components are prepared for homogenization through standard techniques. In a non-limiting embodiment the components are included in the following ranges: 20%-25% Sesquiterpene extract of *juniperus* bark, 2%-4% curcumin treated eugeniacaryophyllata oil, 1%-2% sodium chloride stabilizer, 10%-70% magnesium enriched mineral oil or its aqueous equivalent, 2%-4% 3(trimethoxysilyl) propyl dimethyl octadecyl ammonium chloride, 3%-5%, and mono-saturatedrecinoleic acid. Optionally at least one of water (10%-70%), talc (20-50%), and emulsifier (20-50%) may be included.

The components of the mineral oil or aqueous solution help in containing, carrying and adhering the active ingredients to the surfaces of agriculture or other objects. This also helps in release of other components into the atmosphere while using the invention as a fumigant.

The composition, in varying embodiments, may be applied or a fumigant. It is designed to be configured as oil, liquid, emulsion, aqueous solution, gel, cream, crystal, cakes, powder, granular structures, or a fumigant. Alterations in the ratios of the components enable variations in embodiments. Additional components may be added.

A non-limiting example of an embodiment of the invention in operation involves repelling pests during post-harvest storage in warehouses, packing in food processing units and shipping in boxes or containers. While the various embodiments of the invention may be used for several purposes, one purpose is to protect food even after the cultivation stage.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of e above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning"at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. An improved textile assembly having pest and insect repellent properties, the assembly comprising:

An active ingredient including at least a Terpene; a substrate assembly which is spun bond fabric having a retention backing;

Magnesium enriched mineral oil;

(Hydroxysilyl) Propylmethyloctadecyl Ammonium Chloride; and

Monosaturated recinoleic acid.

2. An improved textile assembly having pest ad insect repellent properties, the assembly comprising:

At least a mineral compound comprising a magnesium-enriched mineral oil or aqueous magnesium;

A Sesquiterpene Extract of *Juniperus* Bark;

Curcumin treated *Eugenia Caryophylla* oil; and

Sodium chloride stabilizer.

3. A complex, comprising, in combination:
- at least an active mineral compound consisting essentially of magnesium enriched mineral oil, 2-(diHydroxysilyl) Propyldimethyloctadecyl Ammonium Chloride, and Monosaturated recinoleic acid;
- terpenes, including at least Sesquiterpene Extract of *Juniperus* Bark, curcumin treated *Eugenia Cacyophyllata* oil, and stabilizers;
- wherein sublimation of the same is effectively managed over time, including with a substrate, to effectively interdict, mitigate or extenuate insect and rodent incursions into food grains over time.

4. A textile assembly having pest and insect repellent properties, which comprises in combination:
- (i) At least a mineral compound;
- (ii) An active ingredient including at least a terpene;
- (iii) A substrate assembly which is spun bond fabric having retention backing;
- (iv) Magnesium enriched mineral oil;
- (v) (Hydroxysilyl)propylmethloctadecyl ammonium chloride; and
- (vi) Monosaturated ricinoleic acid.

5. A textile assembly having pest and insect repellent properties, which comprises in combination:
- (i) At least a mineral compound;
- (ii) An active ingredient including at least a terpene;
- (iii) A substrate assembly which is spun bond fabric having retention backing;
- (iv) A sesquiterpene extract of *Juniperus* bark;
- (v) Curcumin treated *Eugenia Caryophylla* oil; and
- (vi) Sodium chloride stabilizer.

* * * * *